US00PP08329P

United States Patent [19]

van der Knaap

[11] Patent Number: Plant 8,329

[45] Date of Patent: Jul. 27, 1993

[54] CHRYSANTHEMUM PLANT—YELLOW BIJOUX CULTIVAR

[75] Inventor: Jacques C. M. van der Knaap, De Lier, Netherlands

[73] Assignee: Fides Beheer B.V., De Lier, Netherlands

[21] Appl. No.: 721,393

[22] Filed: Jun. 26, 1991

[51] Int. Cl.[5] ..... A01H 5/00

[52] U.S. Cl. ..... Plt./82.2

[58] Field of Search ..... Plt./78, 82.2, 74.1

[56] References Cited

U.S. PATENT DOCUMENTS 4,616,099 10/1986 Sparks ..... 47/58

OTHER PUBLICATIONS

Gosling, ed., 1979, "The Chrysanthemum Manual-6th edition", The National Chrysanthemum Society, London, Essex Telegraph Press, Ltd., pp. 329-336.

Broertjes, et al., 1978, "Application of Mutation Breeding Methods In the Improvement of Vegetatively Propagated Crops", Elsevier Sci. Pub. Co., New York, pp. 162-175.

Broertjes, et al., 1980, "A Mutant of a Mutant of a Mutant of a . . . Irradiation of Progressive Radiation-Induced Mutants in a Mutation Breeding Programme with *Chrysanthemum morifolium*", Euphytica, 29:526-530.

Searle, et al., 1968, "Chrysanthemums the Year Round", Blanford Press, London, pp. 27-29, 320-327.

Chan, 1966, "Chrysanthemum and Rose Mutations Induced by X-Rays", Am. Soc. Hort. Sci. Proc. pp. 613-620.

Broertjes, 1966, "Mutation Breeding of Chrysanthemums", Euphytica, 15:156-162.

Dowrick, et al., 1966, "The Induction of Mutations in Chrysanthemum Using X- and Gamma Radiation", Euphytica, 15:204-210.

*Primary Examiner*—Howard J. Locker

*Attorney, Agent, or Firm*—Burns, Doane, Swecker & Mathis

[57] ABSTRACT

A new and distinct cultivar of Chrysanthemum plant named Yellow Bijoux is provided. The new cultivar was the result of a mutation induced by controlled irradiation with x-rays and can be readily distinguished from the parent Snow Bijoux cultivar (U.S. Ser. No. 721,712, filed concurrently herewith). More specifically, the new cultivar forms attractive yellow flowers of the spider anemone type having a light green center. The yellow tubular ray florets of the Yellow Bijoux cultivar (as illustrated) are substantially different in appearance than those of the Snow Bijoux cultivar which are white. The inflorescence tends to be relatively flat when mature. The response period of the flowers is approximately nine weeks. The new cultivar is particularly suited for use in the production of a cut spider anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Yellow Bijoux.

The new cultivar is a mutation which was induced in a plant of the Snow Bijoux cultivar (U.S. Ser. No. 721,712, filed concurrently herewith) by irradiation with x-rays at a level of 1750 rads. The discovery of the new cultivar was made at De Lier, The Netherlands, during June, 1988. The discovery resulted in the identification of a single plant of the new cultivar.

It was found that the new cultivar of the present invention:

(a) exhibits attractive spider anemone flowers having an overall diameter of approximately 60 mm. wherein the tubular ray florets are yellow and disc florets particularly towards the center of the flower are light green, said flowers being distinguishable from those of the Snow Bijoux cultivar wherein the tubular ray florets are cream white, (b) bears flowers in a generally flat capitulum form when mature, (c) exhibits a flower response period of approximately nine weeks, (d) forms attractive dark green foliage, and (e) has the ability to produce flowers of commercially acceptable quality throughout the year in a cut mum production program.

Asexual reproduction of the new cultivar by cuttings performed at De Lier, The Netherlands, in a controlled environment has demonstrated that the characteristics of the new cultivar as herein disclosed are firmly fixed and are retained through successive generations of asexual propagation.

Yellow Bijoux has not been observed under all possible environmental conditions to date. Accordingly, it is possible that the phenotype may vary somewhat with variations in the environment, such as temperature, light, day length, contact with pesticides and/or subjection to growth retardant treatments.

The new Yellow Bijoux cultivar can be distinguished from the parent Snow Bijoux cultivar in several significant respects. As previously indicated, the flowers of the Yellow Bijoux cultivar possess ray florets that are yellow in coloration as well as light green disc florets which gradually change to yellow upon maturation. In contrast, the flowers of the Snow Bijoux cultivar possess white ray florets and disc florets that are white upon maturation. Following detailed observation it has been determined that the flower diameter of the Yellow Bijoux cultivar commonly is somewhat smaller than that of the Snow Bijoux cultivar when produced under the same growing conditions. For instance, it has been found that flower diameter of the Yellow Bijoux cultivar commonly is approximately 60 mm. while that of the Snow Bijoux cultivar commonly is approximately 65 mm. Additionally, it has been found that the new Yellow Bijoux cultivar is less vegetative than the parent Snow Bijoux cultivar.

When the new cultivar of the present invention is compared to the parent of the Snow Bijoux cultivar (i.e., the Bijoux cultivar of U.S. Plant Pat. No. 6,241), it is found that the parent Bijoux cultivar exhibits tubular ray florets which are of a dissimilar soft pink coloration.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of The Royal Horticultural Society, London, England. The color values were determined at 11:00 a.m. to 12:00 noon under natural daylight conditions at De Lier, The Netherlands, during October, 1989. The plants described were grown under standard greenhouse conditions which approximate those commonly utilized for the production of cut mums.

Classification:

*Botanical.*—*Chrysanthemum morifolium* Ramat., cv. Yellow Bijoux.

*Commercial.*—Cut spider anemone spray.

Inflorescence

A. Capitulum:

*Form.*—Generally flat when mature.

*Type.*—Spider anemone.

*Diameter across face.*—Approximately 60 mm. on average.

B. Corolla of ray and disc florets:

*Color (General tonality from a distance of three meters).*—Yellow with some darkening at center.

*Color ray florets (top surface).*—Yellow, Yellow-orange group 14C.

*Color disc florets.*—Light green, approaching Green-white group 157B on the exposed distal ends.

C. Reproductive organs:

*Androecium.*—Only rudimentary in disc florets.

*Gynoecium.*—Present in both ray and disc florets.

Plant

A. General appearance:

*Height.*—Approximately 80 cm. on average.

B. Foliage:

*Color (upper surface).*—Yellow-green group 147A.

*Color (under surface).*—Yellow-green group 147B.

I claim:

1. A new and distinct cultivar of Chrysanthemum plant named Yellow Bijoux, substantially as herein shown and described, which:

(a) exhibits attractive spider anemone flowers having an overall diameter of approximately 60 mm. wherein the tubular ray florets are yellow and the disc florets particularly towards the center of the flower are light green, such flowers being distinguishable from those of the Snow Bijoux cultivar wherein the ray florets are cream white, (b) bears flowers in a generally flat capitulum form when mature, (c) exhibits a flower response period of approximately nine weeks, (d) forms attractive dark green foliage, and (e) has the ability to produce flowers of commercially acceptable quality throughout the year in a cut mum production program.

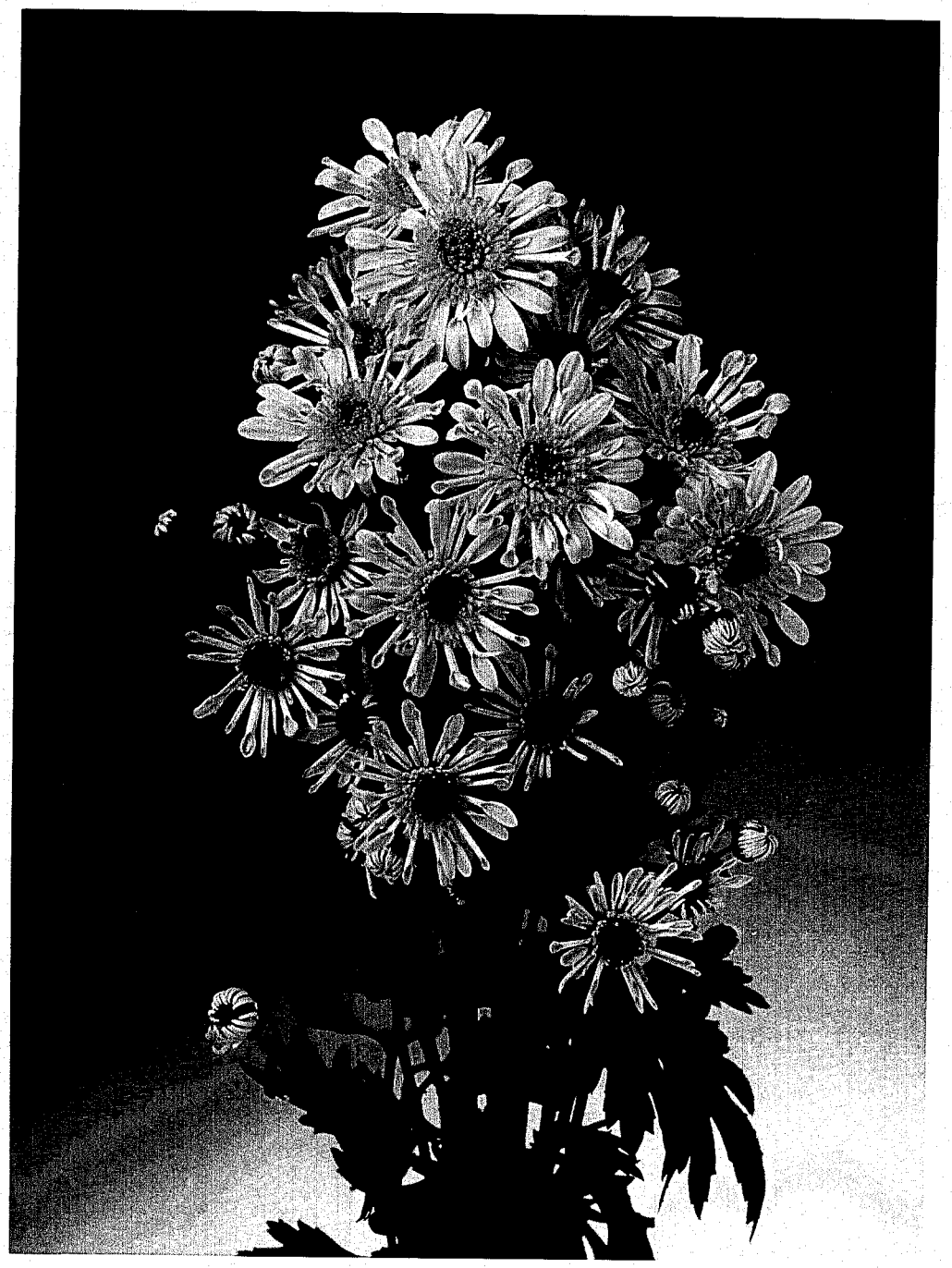

* * * * *